United States Patent [19]

Bennington

[11] 3,958,571

[45] May 25, 1976

[54] SWAB APPLICATOR

[76] Inventor: William E. Bennington, 5 Fillmore Drive, Sarasota, Fla. 33578

[22] Filed: Aug. 22, 1973

[21] Appl. No.: 390,404

[52] U.S. Cl. ............................. 128/269; 401/198
[51] Int. Cl. .................................... A61M 35/00
[58] Field of Search ............ 128/269; 401/177, 198, 401/199, 132

[56] References Cited
UNITED STATES PATENTS

| | | | |
|---|---|---|---|
| 1,309,201 | 7/1919 | Hollister | 128/269 |
| 3,519,364 | 7/1970 | Truhan | 128/269 X |
| 3,661,666 | 5/1972 | Foster et al. | 128/269 X |
| 3,757,782 | 9/1973 | Aiken | 128/269 |
| 3,759,259 | 9/1973 | Truhan | 128/269 |

*Primary Examiner*—Lawrence Charles
*Attorney, Agent, or Firm*—Millen, Raptes & White

[57] ABSTRACT

The invention relates to a swab applicator which comprises an elongated hollow tube open at one end, normally closed at the opposite end, and containing a solution such as a medicament. A swab of absorbent material is secured around the open end, and the opposite end is provided with means to open the end to permit the solution to flow by gravity into said swab.

12 Claims, 8 Drawing Figures

U.S. Patent    May 25, 1976    3,958,571
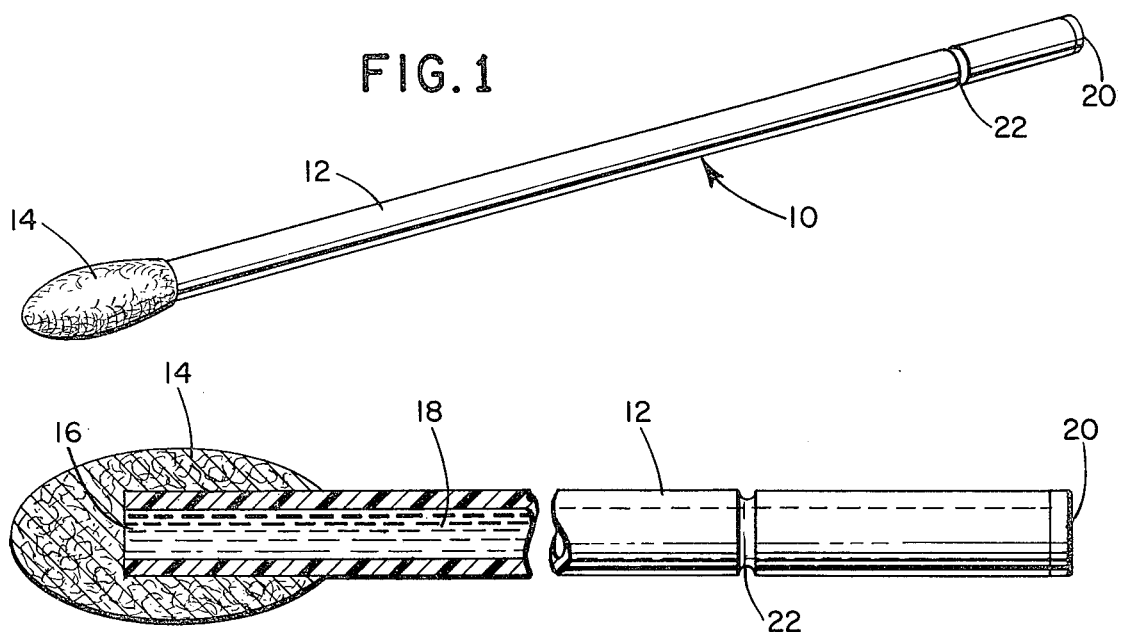
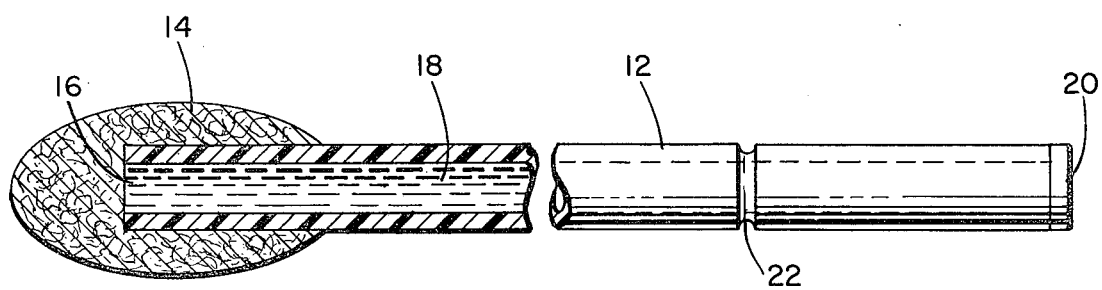
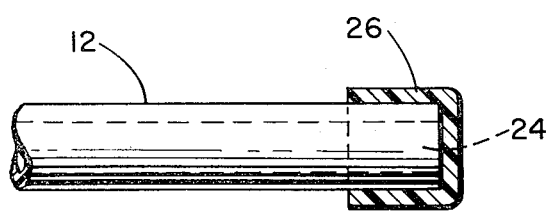    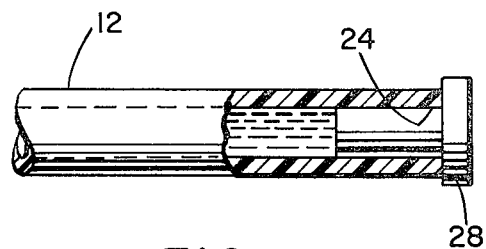
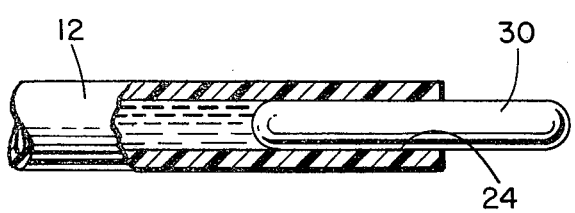    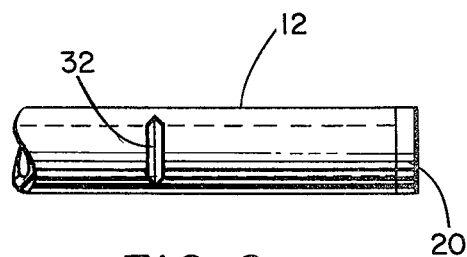
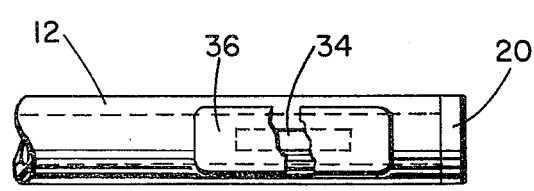    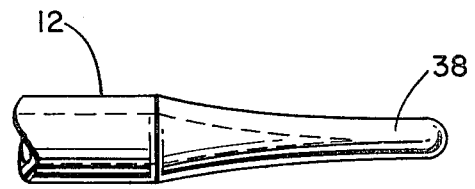

SWAB APPLICATOR

BACKGROUND OF THE INVENTION

This invention relates to improvements in swab applicators and more particularly to medicated swab applicators.

Various types of swab applicators are known such as those with an absorbent wad of material on the ends of a stick. The absorbent material, usually cotton, is dipped in a medicament and applied where needed. Other types of applicators comprise a hollow tube containing a solution to be applied, a plunger at one end, and a swab at the other end into which the solution is forced by the plunger such as the one shown in U.S. Pat. No. 3,519,364. Other devices such as in U.S. Pat. No. 1,309,201 include enclosed glass tubes containing the solution to be applied, wherein, upon use an end portion of the tube is broken to permit the solution to flow by gravity into a swab. Although, the above applicators perform the intended function, the devices are somewhat complicated and relatively expensive to produce.

BRIEF SUMMARY OF THE INVENTION

It is an object of this invention to provide a simple, inexpensive swab applicator containing a solution to be applied.

Another object of this invention is to provide a swab applicator, an elongated hollow tube containing the solution to be applied.

A further object of this invention is to provide a swab applicator comprising an elongated hollow tube open at one end and containing the solution to be applied, and provided with means for permitting the solution to drain from the open end of the tube, when desired, into a swab.

Other and further advantages of the invention will be apparent from the following description and claims taken together with the drawings.

DETAILED DESCRIPTION OF THE INVENTION

Referring to the drawings:

FIG. 1 is a perspective view of the swab applicator of this invention;

FIG. 2 is a side elevational view of the swab applicator;

FIGS. 3, 4, 5, 6, 7, and 8 are enlarged side elevational view of one end of the swab applicator showing six embodiments of the means for releasing the solution from the hollow tube.

Referring to the drawings and in particular FIGS. 1 and 2, the numeral 10 generally denotes the swab applicator of the invention comprising a hollow capillary tube 12 and a cotton swab 14. The tube 12 is open at the end 16 over which the swab 14 is secured. The tube is prefilled with a solution 18 which may be a medicament such as iodine, merthiolate, baby oil, or any other type of solution which can be swabbed onto a surface from a swab. The opposite end 20 of the tube is sealed. Accordingly, the solution is retained in the tube by capillary action. The tube is provided with means for permitting the solution to flow into the swab when use thereof is desired. In FIG. 2 the means comprises a declevity 22 about one half inch from the closed end 20. At the declevity, the tube can easily be broken thereby equalizing the pressure and allowing the solution 18 to flow by gravity into the cotton swab through open end 16. If the solution does not flow immediately, the tube can be shaken slightly and thereby the solution will flow easily into the swab.

FIGS. 3, 4, 5, 6, 7, and 8 show modifications of the means for equalizing the pressure in the tube thereby permitting the solution to flow into the swab. Thus, in FIG. 3, the tube 12 has an open end 24 around which a cylinder cap 26 is press fitted.

FIG. 4 shows a cylinder cap 28 which is press fitted into the open end 24 of the tube. Removal of caps 26 and 28 will permit the solution to flow into the swab.

In FIG. 5, a rigid rod 30 is fitted into the open end 24 of tube 14 and is either press fitted or sealed by suitable means therein. In this embodiment, the rod 30 is used to break off the end of the tube 12 to equalize the pressure.

FIG. 6 shows an embodiment wherein the end 20 of the tube 14 is closed, as in the embodiment in FIG. 2. The tube is grooved or scored at 32, which permits the tube to be easily broken to equalize the pressure.

FIG. 7 discloses still another suitable embodiment wherein the end 20 of the tube is closed, as in the embodiment of FIG. 2. The tube is provided with a slit 34 covered by an adhesive tab 36. Removal of tab 36 equalizes the pressure and permits the solution to drain from the opposite open end into the swab.

In FIG. 8, the end of the tube 12 is formed to a fine point 38. It is only necessary to snap or fracture the point 38 thereby equalizing the pressure and permitting the solution to flow out the opposite open end into the swab.

The above described means for equalizing the pressure and permitting the solution to drain from the tube are only a few of the possible means. Thus, the closed end 20 of tube 12 could be snipped off with a pair of scissors.

One of the advantages of this invention is that it makes it possible to produce an inexpensive swab applicator. Thus, tube 12 can be a plastic tube of thin walled, structurally firm, construction which does no sacrifice the functional advantages of the applicator. The tube can also be constructed of glass, metal and the like.

The swab 14 is a wad of fibrous material such as cotton or a sponge material which is wound or secured around the open end 16 of the tube. The end of the tube 16 can also be provided with lateral holes (not shown) near the end 16 to facilitate impregnation of the swab by the solution.

The tube 12 is prefilled at the factory to contain the solution of medicament, etc., and the solution is retained in the tube by the fact that the opposite end is closed as described heretofore. Upon use, the opposite end is opened by the various means described and the solution drains by gravity into the swab. The applicator is produced to contain enough solution for a one time application and can then be discarded. The tube can be made in various sizes of diameters and lengths for various uses.

The closure means 26, 28 and 30 shown in FIGS. 3, 4 and 5, respectively, can be made of various soft materials such as rubber, plastic, etc., which are inert to the solution in the applicator.

Although tube 12 has been depicted as a hollow tube, it is understood that the invention contemplates the use of a hollow member having various types of cross-sectional configurations, i.e., polyganol cross-sections such as triangular, square, pentagonal, etc. as well as fluted sections. In addition, it is within the concept of this invention to provide an elongated hollow member divided into two or more longitudinal sections, each of which can contain separate distinct solutions which can mix and/or react together when they drain into the swab 14. This type of combination is useful in analytical procedures wherein separate known indicator solutions from the tube will react in the swab, which is then applied to an unknown solution, surface, or compound to be analyzed.

Having now described the invention in specific detail and exemplified the manner in which it may be carried into practice, it will be readily apparent to those skilled in the art that innumerable variations, applications, modifications, and extensions of the basic principles involved may be made without departing from its spirit or scope.

What is claimed is:

1. A swab applicator comprising a structurally firm, elongated, hollow capillary member, one end of said capillary member being open and being surrounded with an absorbent swab secured thereto, wherein said end opening is embedded in said swab, the opposite end of said capillary member being normally closed, said capillary member being prefilled throughout a substantial portion thereof with a usable solution, said solution being retained within said capillary member by capillary action and by said closed end, opening means disposed at said closed end for easy opening of said closed end, whereby upon opening, pressure is equalized at both ends of said capillary member, and whereby a substantial portion of said solution will drain into said swab and be absorbed therein.

2. The applicator of claim 1 wherein said hollow member is tubular and said swab is cotton.

3. The applicator of claim 1 wherein said opposite end is open and normally contains a closure cap which surrounds said open end and which can be removed to open said opposite end.

4. The applicator of claim 1 wherein said opposite end is open and normally contains a closure cap which is inserted in said open end, and which cap can be removed to open said opposite end.

5. The applicator of claim 1 wherein said opposite end is open and normally contains a rigid rod secured within said opening, and which rod can be used to fracture and open said opposite end.

6. The applicator of claim 1 wherein said opposite end comprises a slot near said end containing an adhesive closure thereover, and which closure can be removed to open said normally closed end.

7. The applicator of claim 1 wherein said opposite end comprises a transverse groove near said end, and which groove is used to fracture and open said opposite end.

8. The applicator of claim 1 wherein said opposite end is normally closed as a tapering point, and which point is used to fracture and open said opposite end.

9. The applicator of claim 1 wherein said opposite end comprises a declevity near said end, and which declevity is used to fracture and open said opposite end.

10. The applicator of claim 1 wherein said hollow member is polyganol in cross section.

11. The applicator of claim 1 wherein said hollow member is cylindrical in cross section.

12. The applicator of claim 1 wherein said hollow member comprises at least two longitudinal sections, each section of which contains a separate distinct solution.

* * * * *